US010882887B2

(12) United States Patent
Xu et al.

(10) Patent No.: US 10,882,887 B2
(45) Date of Patent: Jan. 5, 2021

(54) PAPILLOMAVIRUS CHIMERIC PROTEIN AND APPLICATION THEREOF (71) Applicant: Institute of Basic Medical Sciences, Chinese Academy of Medical Sciences, Beijing (CN)

(72) Inventors: Xuemei Xu, Beijing (CN); Xue Chen, Beijing (CN); Ting Zhang, Beijing (CN); Zhirong Wang, Beijing (CN); Hongyang Liu, Beijing (CN); Shuo Wang, Beijing (CN); Meili Hu, Beijing (CN)

(73) Assignee: INSTITUTEOF BASIC MEDICAL SCIENCES, CHINESE ACADEMY OF MEDICAL SCIENCES, Beijing (CN)

( * ) Notice: Subject to any disclaimer, the term of this patent is extended or adjusted under 35 U.S.C. 154(b) by 193 days.

(21) Appl. No.: 16/129,348

(22) PCT Filed: Mar. 2, 2017

(86) PCT No.: PCT/CN2017/075402
§ 371 (c)(1),
(2) Date: Sep. 12, 2018

(87) PCT Pub. No.: WO2017/157173
PCT Pub. Date: Sep. 21, 2017

(65) Prior Publication Data
US 2019/0031724 A1  Jan. 31, 2019

(30) Foreign Application Priority Data
Mar. 15, 2016 (CN) .......................... 2016 1 0146109

(51) Int. Cl.
| C07K 14/01 | (2006.01) |
| C07K 14/025 | (2006.01) |
| A61K 39/12 | (2006.01) |
| C12N 15/62 | (2006.01) |
| C12N 15/70 | (2006.01) |
| C07K 14/005 | (2006.01) |
| C12N 15/63 | (2006.01) |
| C07K 19/00 | (2006.01) |
| A61P 31/20 | (2006.01) |
| A61K 39/00 | (2006.01) |

(52) U.S. Cl.
CPC ............ *C07K 14/005* (2013.01); *A61K 39/12* (2013.01); *A61P 31/20* (2018.01); *C07K 19/00* (2013.01); *C12N 15/63* (2013.01); *A61K 2039/5258* (2013.01); *A61K 2039/575* (2013.01); *C12N 2710/20022* (2013.01); *C12N 2710/20034* (2013.01)

(58) Field of Classification Search
None
See application file for complete search history.

(56) References Cited

FOREIGN PATENT DOCUMENTS

| CN | 1976718 A | 6/2007 |
| CN | 101518647 | 9/2009 |
| CN | 102497880 A | 6/2012 |
| CN | 101148661 | 1/2013 |
| CN | 101293918 B | 3/2013 |
| CN | 104418942 | 3/2015 |
| WO | 2005123125 | 12/2005 |
| WO | 2010149752 | 12/2010 |
| WO | WO-2010149752 A2 * | 12/2010 ............... C12N 7/00 |

OTHER PUBLICATIONS

Schellenbacher et al. Efficacy of RG1-VLP Vaccination against Infections with Genital and Cutaneous Human Papillomaviruses. Journal of Investigative Dermatology (2013) 133, 2706-2713.*
Boxus, M. et al., "Broad Cross-Protection Is Induced in Preclinical Models by a Human Papillomavirus Vaccine Composed of L1/L2 Chimeric Virus-Like Particles" J. Virology, May 4, 2016, vol. 90, 6314-6325.
Chang, X. et al. "Human papilloma virus preventive vaccine, construction method and application" Chinese Patent Application Publication 101518647, Sep. 2, 2009, English Abstract.
Gambhira, R. et al., "A Protective and Broadly Cross-Neutralizing Epitope of Human Papillomavirus L2", J. Virology, Oct. 10, 2007, vol. 81, 13927-13931.
Schellenbacher, C. et al., "Chimeric L1-L2 Virus-Like Particles as Potential Broad-Spectrum Human Papillomavirus Vaccines" J. Virology, Jul. 29, 2009, vol. 83, 10085-10095.
Seitz, H. et al., "A three component mix of thioredoxin-L2 antigens elicits broadly neutralizing responses against oncogenic human papillomaviruses" Vaccine, Mar. 21, 2014, vol. 32, 2610-2617.
Tumban, E et al. "A Pan-HPV Vaccine Based on Bacteriophage PP7 VLPs Displaying Broadly Cross-Neutralizing Epitopes from the HPV Minor Capsid Protein, L2" PLOS ONE, Aug. 17, 2011, vol. 6, e23301, 1-11.

(Continued)

Primary Examiner — Nianxiang Zou
(74) Attorney, Agent, or Firm — Harvest IP Law LLP (57) ABSTRACT Provided is a papillomavirus chimeric protein, the skeleton thereof being a papillomavirus L1 protein or a mutant thereof, at least one human papillomavirus 33-type L2 protein or mutant polypeptide thereof being embedded on the skeleton. The present papillomavirus chimeric protein can be used for preparing a vaccine for preventing papillomavirus infections and infection induced disease.

12 Claims, 3 Drawing Sheets
Specification includes a Sequence Listing.

(56) References Cited

OTHER PUBLICATIONS

Nieto, K. et al., "Development of AAVLP(HPV16/31L2) Particles as Broadly Protective HPV Vaccine Candidate" PLOS ONE, Jun. 27, 2012, vol. 7, e39741, 1-12.

Huber, B. et al., "A Chimeric 18L1-45RG1 Virus-Like Particle Vaccine Cross-Protects against Oncogenic Alpha-7 Human Papillomavirus Types" PLOS ONE, Mar. 19, 2015, vol. 10, e0120152, 1-18.

Castellsague, X. et al., Vaccine 25S (2007) C1-C26.

Kondo, K. et al., "Modification of Human Papillomavirus-Like Particle Vaccine by Insertion of the Cross-Reactive L2-Epitopes" J. Medical Virology, 2008, vol. 80, 841-846.

Schellenbacher, C. et al., "Efficacy of RG1-VLP Vaccination against Infections with Genital and Cutaneous Human Papillomaviruses", J. Investigative Dermatology, Jun. 27, 2013, 253, 1-8.

Touze. A. et al. "The L1 Major Capsid Protein of Human Papillomavirus Type 16 Variants Affects Yield of Virus-Like Particles Produced in an Insect Cell Expression System" J. Clinical Microbiology, 1998, vol. 36, 2046-2051.

Gu, Y. et al., "Shorten human papilloma virus 16 type L1 protein", Chinese Patent 1012939188, Mar. 27, 2013, English Abstract.

Xu, X. et a;., "Human papilloma virus 16 type coat protein virus-like particles, preparation method and use thereof" Chinese Patent 1011486618, Jan. 2, 2013, English Abstract.

Kong, W. et al. "Truncated L1 proteins of human papilloma virus (HPV), virus-like particles as well as preparation method and application of virus-like particles" Chinese Patent Application Publication 104418942, Mar. 18, 2015, English Abstract.

\* cited by examiner

PAPILLOMAVIRUS CHIMERIC PROTEIN AND APPLICATION THEREOF

CROSS REFERENCE TO RELATED APPLICATIONS

This application claims the benefits under 35 U.S.C. § 371 of International Application Number PCT/CN2017/075402, filed on Mar. 2, 2017, which claimed priority to the Chinese Patent Application No. 201610146109.5, filed on Mar. 15, 2016.

FIELD OF THE INVENTION

The present invention relates to the field of biology and medicine, in particular, to a chimeric papillomavirus (PV) protein, a virus-like particle (VLP) composed of said chimeric PV protein, and to the use of the chimeric PV protein or the chimeric PV VLP in the preparation of the vaccine for preventing PV infection and the diseases associated with the infections.

BACKGROUND OF THE INVENTION

Over 200 types of human papillomavirus (HPV) have been identified, all of which are classified as mucosal or cutaneous HPVs. Mucosal HPVs mainly infect the mucosa and skins of urogenital tract, anus, crissum and oropharynx, and induce various benign and malignant lesions. According to the diseases induced, mucosal HPVs are classified as oncogenic high-risk types (comprising HPV 16, -18, -31, -33, -35, -39, -45, -51, -52, -56, -58, -59, -68, etc.), probably high-risk types (HPV 26, -30, -53, -66, -67, -69, -70, -73, -82, -85, etc.), undetermined types (HPV 34, -42, -43, -54, -71, -81, -83, -97, -102, -114, etc.), and low-risk types (HPV 6, -7, -11, -13, -32, -40, -42, -44, -61, -62, -72, -74, -81, -83, -84, -86, -87, -89, -90, -91, -106, etc.) which induce benign lesions such as verrucous hyperplasia. Cutaneous HPVs mainly infect skins from the sites other than above-mentioned, and induce skin verrucous hyperplasia. The infection of cutaneous HPVs also closely related to some skin cancers.

Malignant tumors associated with high-risk HPVs (HR-HPVs) include carcinoma of cervix, vagina, vulva, penis, anus, crissum, oropharynx, tonsil, oral, etc., among which cervical cancer is the most harmful. It is the third prevalent cancer in women all over the world. An estimated 527,000 cases of cervical cancer occur worldwide every year, among which 285,000 cases occur in Asia, and 75,000 cases in China.

HPV16 is the most prevalent type all over the world, the detection rate of which ranks the first in HPV associated cancers and precancer lesions of cervix, crissum, penis, vulva, etc. For example, cervical cancers associated with HPV16 infection accounts for 58.7% cervical cancers in China and 53.5% cervical cancers worldwide, while other 19 HR-HPVs infection accounts for the rest 41.3%-46.5% cervical cancers together. Until present, several prophylactic HPV vaccines have been approved, all of which are based on virus-like particle (VLP) of HPV L1 protein, including bivalent Cervarix (HPV16/18) of GSK, and quadrivalent Gardasil (HPV6/11/16/18) and nonavalent Gardasil 9 (HPV6/11/16/18/31/33/45/52/58) of Merck. The protective immune responses induced by such vaccines are mainly directed to the types of vaccine components, therefore, these vaccines are mostly HPV polyvalent vaccines. To obtain the preventive effect of broad-spectrum vaccines, it is necessary to continue to expand the types of vaccine components.

Since more than 200 types of HPVs and 20 types of HR-HPVs have been identified, it is a great challenge to develop broad-spectrum HPV vaccines by simply increasing the types of VLPs, considering both economical cost and tolerable dose limit.

The minor capsid protein L2 can induce cross-neutralizing antibodies and cross-protection responses in vivo. It is reported that the neutralizing epitopes which induce the cross-protection responses mainly located in several conservative regions of the N-terminus of L2 protein. For example, the immune sera of the polypeptide of amino acid (aa.) 17-36 of HPV16 L2 protein can neutralize HPV16/18 at a high titer, and also effectively neutralize HPV 5/6/45/52/58 (Gambhira R, Karanam B, et al. J. Virol. 2007; 81(24): 13927-13931). A monoclonal antibody RG-1, which binds to aa. 17-36 of HPV16 L2 protein, also has cross-neutralizing activity (Gambhira R, Karanam B, et al. J. Virol. 2007; 81(24): 13927-13931). Thus the regions homologous to HPV16 L2 aa. 17-36 polypeptide on L2 proteins are named as RG-1 epitopes.

HPV16 L2 aa. 17-36 polypeptide-based fusion protein vaccine, which is constructed with different vaccine scaffold, such as thioredoxin (Trx), bacteria phage VLP, plant virus VLP, and mammalian viruses VLP (adeno-associated virus, bovine papilloma virus-1, HPV16), can significantly improve the immunogenicity of polypeptide, increase the titer of neutralizing antibody and broaden the protective spectrum (Christina S, Richard R, et al. J. Virol. 2009; 83(19):10085-10095; Seitz H, Canali E, et al. Vaccine 2014; 32: 2610-2617; Tumban E, Peabody J, et al. PLoS One 2011; 6(8): e23310; Nieto K, Weghofer M, et al. PLoS One 2012; 7(6): e39741).

The polypeptide region of HPV L2 aa. 17-36 shares high amino acid sequence homology between different types of papillomaviruses. Reports about the vaccines based on RG-1 epitope from various types of HPVs are listed below: inserting HPV31/51 RG-1 epitopes into the surface region of bacteria Trx protein, the resulting immune sera possesses cross-neutralizing activity, but can only neutralize a few types (Seitz H, Canali E, et al. Vaccine 2014; 32: 2610-2617); inserting HPV16/31 RG-1 epitopes into the surface region of adeno-associated virus VLP, the resulting immune sera neutralize 6 types of HPVs in total (Nieto K, Weghofer M, et al. PLoS One 2012; 7(6): e39741); inserting HPV45 RG-1 epitope into the surface region of HPV18 VLP, the resulting immune sera neutralized 4 types of HPVs in total (Huber B, Schellenbacher C, et al. PLoS One 2015; 10(3): e0120152). The results indicate that all the RG-1 epitopes mentioned above can induce cross-neutralizing antibodies. Furthermore, when inserting the truncated polypeptides of RG-1 regions from different types (HPV1/5/6/11/16/18/45/58 L2 aa. 17-31) into the surface of phage VLPs, respectively, and immunizing mice with the resulting 8 chimeric VLPs (cVLPs), protective immunities were detected against 8 types of viruses (Tumban E, Peabody J, et al. PLoS One 2011; 6(8): e23310). However, due to the lack of specific analysis of the immunogenicity of each truncated RG-1 polypeptide cVLP, the immunogenicity of each RG-1 epitope is unknown. From the analyses of the types of neutralizing in the above literature, the immunogenicity of HPV16 RG-1 epitope is the strongest. Whether inserted into the surface of HPV or bacteriophage VLP, it can both induce broad-spectrum neutralizing antibody responses. The immunogenicity of HPV31/45/51 RG-1 epitopes may rank after HPV16, and the immunogenicity of other types of RG-1 epitopes is unknown (not reported). It is worth noting that, when immunizing with 8 bacteriophage cVLPs containing 
different truncated polypeptides (L2 aa. 17-31) of RG-1 region (HPV1/5/6/11/16/18/45/58) simultaneously, the neutralizing spectrum of immune sera is relatively narrow, suggesting that some of the truncated polypeptides used here possess no or weak immunogenicity. The specific comparison of the immunogenicity of different types of RG-1 epitope polypeptides and the truncated polypeptides is expected to clarify the immunogenicity and the differences in immunogenicity. Except for HPV16, the immunogenicity of RG-1 epitope regions from other different types is currently under researched or lacks research. Besides, the immunogenicity of different types of RG-1 epitope regions has not been comparatively analyzed. Most importantly, in the studies regarding vaccines the selection of the types of RG-1 epitopes are not based on the immunogenicity, but on other factors such as the prevalence of the type of viruses and the severity of infection-associated diseases. Thus, current studies regarding RG-1 epitope-based vaccines should be improved.

Infection rate and detection rate of HPV33 in HPV-related tumors are relatively high. In the world, its detection rate in cervical cancer specimens was 2.6%, and 3.8% in Asia and China, which only ranks after HPV16/18/58 (X. Castellsague et al. Vaccine 25S (2007) C1-C26). However, the immunogenicity of the RG-1 epitope of the HPV33 L2 protein has not been studied. Whether HPV33 RG-1 epitope can induce neutralizing antibody is still unknown, and the spectrum and characteristic of the induced neutralizing antibody has not been analyzed either. Thus the immunogenicity of HPV33 RG-1 epitope-based vaccines cannot be predicted according to available studies.

It is reported that HPV16 L1 VLP is a promising scaffold for HPV16 L2 RG-1 epitope-based vaccine. After inserting HPV16 L2 RG-1 epitope at specific sites on the surface region of HPV16 L1 VLP by proper methods, HPV16 L2 RG-1 epitope can be displayed on the surface of VLP, and induce broad-spectrum neutralizing antibodies and protective responses after immunization. For example, directly inserting HPV16 L2 aa. 17-36 into the site on DE loop of HPV16 L1 protein (between aa. 136/137), the resulting chimeric VLPs (cVLP) can induce broad-spectrum neutralizing antibody responses, and can neutralize at least 14 HPV types (Schellenbacher C, Roden R, et al 2009; J. Virol. 2009; 83(19): 10085-10095). When replacing amino acids between 430/433 on h4 region with HPV16 L2 aa. 18-38 by non-equal length substitution, the resulting cVLP can induce cross-neutralizing antibodies against HPV18 and HPV31 (Kondo K, Ochi H, et al. J. Med. Virol. 2008; 80:841-846). There is no report on inserting HPV33 L2 protein epitope into the surface of papillomavirus VLPs until present. Since the sequence of HPV33 RG-1 epitope is different from that of HPV16 RG-1 epitope (about 80% homology), it is unknown whether the VLPs can be formed after inserting the epitope into the sites mentioned above. Moreover, when using other inserting methods, such as inserting the epitopes by non-equal length substitution at 135-138 of DE loop region and introduce amino acid modification at both ends of inserted fragment, it is not elucidated whether the inserted epitope can be presented on the surface of VLP, and whether such insertion will affect the formation of major neutralizing epitope on VLP backbone is also unclear. Finally, after inserting truncated HPV33 L2 polypeptide into above-mentioned regions, whether the resulted fusion protein can form VLP, whether the formed VLP can induce cross-protection responses, whether the insertion will have any impact on the major neutralizing epitope, and whether it will affect the expression level, are all unclear. The above unclear issues are unpredictable.

Therefore, the present invention uses HPV33 RG-1 epitope and truncated RG-1 epitopes for the study of HPV16 cVLP. The results show that the HPV33 RG-1 long epitope and short epitope cVLPs are highly immunogenic (can neutralize at least 10 HPV types), and the immunogenicity of which is comparable to that of the reported HPV16 RG-1 cVLP, but the neutralizing spectrums of these cVLPs are different (Schellenbacher C, Roden R, et al 2009; J. Virol. 2009; 83(19): 10085-10095; Schellenbacher C, Kwak K, et al. J. Invest. Derma. 2013; doi:10.1038/jid.2013.253).

SUMMARY OF THE INVENTION

In view of the above, the object of the present invention is to provide a chimeric papillomavirus (PV) protein for use in the preparation of a vaccine for the prevention of papillomavirus infection and the infection-associated diseases.

The inventors have surprisingly found that the insertion of the polypeptide of HPV33 L2 protein into the surface region of a full-length or truncated form of HPV16 L1 protein enhances the immunogenicity of HPV33 L2 polypeptide, and the resulting chimeric protein can be highly expressed in the expression systems of *E. coli* or insect cell. The chimeric protein can be assembled into VLPs and elicit broad-spectrum protective immune responses against multiple types of HPVs from different genus/subgenus. The present invention is based on the above findings and has now been completed to provide data in the examples herein.

Based on the above purposes, in one aspect, the present invention provides a chimeric papillomavirus protein comprising a scaffold which is a PV L1 protein or a mutant of the PV L1 protein, and at least one polypeptide derived from HPV33 L2 protein is inserted into said scaffold.

Optionally, said polypeptide is selected from any fragment of the consecutive 8-33 amino acids within the region of amino acid (aa.) position 1-200 of the HPV33 L2 protein (amino acid sequence shown as SEQ ID No. 7). Further preferably, the polypeptide is derived from HPV33 L2 RG-1 epitope region.

Preferably, the amino acid sequence of the polypeptide is shown as SEQ ID No. 1.

Optionally, the polypeptide is a polypeptide obtained by extending or truncating 1-5 amino acids from the sequence shown as SEQ ID No. 1 at the N-terminus and/or at the C-terminus.

Preferably, the amino acid sequence of the polypeptide is shown as SEQ ID No. 2 or SEQ ID No. 3.

Optionally, the polypeptide may also be a polypeptide having a homology of greater than 60% with the amino acid sequence shown as SEQ ID No. 1, preferably a polypeptide having a homology of greater than 70%, greater than 80%, greater than 90%, and even more preferably greater than 95% with the amino acid sequence shown as SEQ ID No. 1.

Optionally, the scaffold is HPV16 L1 protein or a mutant of the HPV16 L1 protein.

Preferably, said HPV16 L1 protein is selected from HR-HPV L1 proteins or the mutants of the HR-HPV L1 proteins. Further preferably, the scaffold of the chimeric protein of present invention is selected from HPV16 L1 proteins (e.g. the sequence of NCBI database AAC09292.1) or the mutants of the HPV16 L1 proteins. The HPV16 L1 protein scaffold can be derived from, but not limited to, the L1 protein of HPV16 Phi1, Tha1, Alg1, Sen32, Fra25, Fra63, 114K, 114B, Z-1194 variants (Touze A, Mehdaoui S E, et al.

J. Clin. Micr. 1998; 36(7): 2046-2051). Preferably, the amino acid sequence of the HPV16 L1 protein is shown as SEQ ID No. 4.

Optionally, the mutant of HPV16 L1 protein is obtained by truncating 0-9 amino acids at the N-terminus from the HPV16 L1 protein and/or truncating 0-34 amino acids at the C-terminus from the HPV16 L1 protein.

Optionally, the HPV33 L2 protein-derived polypeptide is inserted into the surface region of HPV16 L1 protein or of the mutant of the HPV16 L1 protein with a 31-amino-acid truncation at the C-terminus, preferably, into the DE loop of said HPV16 L1 protein or said mutant of the HPV16 L1 protein with a 31-amino-acid truncation at the C-terminus. Still more preferably, the HPV33 L2 protein-derived polypeptide is directly inserted into said HPV16 L1 protein or of said mutant of HPV16 L1 protein with a 31-amino-acid truncation at the C-terminus, between the amino acid position 136 and 137 thereof, or is inserted by non-equal length substitution at aa. 135-138 region of said HPV16 L1 protein or of the mutant of HPV16 L1 protein with a 31-amino-acid truncation at the C-terminus; wherein, in the embodiment of non-equal length substitution, HPV33 L2 protein-derived polypeptide contains linker(s) of 1-3 amino acid(s) at its N-terminus and/or C-terminus.

Optionally, said linker consists of any combination of amino acid(s) selected from the group consisting of glycine (G), serine (S), alanine (A) and proline (P). Preferably, the sequence of the N-terminal linker is "G (glycine) P (proline)" and the sequence of the C-terminal linker is "P (proline)".

Optionally, in the embodiment of direct insertion, the amino acid sequence of the HPV33 L2 protein-derived polypeptide is shown as SEQ ID No. 1 or SEQ ID No. 2, and the insertion site is between the amino acid position 136 and 137 of said HPV16 L1 protein or of said mutant of the HPV16 L1 protein with a 31-amino-acid truncation at the C-terminus.

Optionally, in the embodiment of the non-equal length substitution, after the deletion of the amino acid 135-138 region of said HPV16 L1 protein or of the mutant of HPV16 L1 protein with a 31-amino-acid truncation at the C-terminus, the polypeptide of the amino acid sequence SEQ ID No. 5 or SEQ ID No. 6 is inserted between the amino acid 134 and 139 of said HPV16 L1 protein or the mutant of HPV16 L1 protein with a 31-amino-acid truncation at the C-terminus.

Optionally, the HPV33 L2 protein-derived polypeptide is inserted into the surface region of HPV16 L1 protein or of the mutant of the HPV16 L1 protein with a 31-amino-acid truncation at the C-terminus, preferably, into the h4 region of said HPV16 L1 protein or said mutant of HPV16 L1 mutant protein with a 31-amino-acid truncation at the C-terminus. More preferably, the HPV33 L2 protein-derived polypeptide is inserted by non-equal length substitution at aa.431-432 region of said HPV16 L1 protein or the mutant of the HPV16 L1 protein with a 31-amino-acid truncation at the C-terminus. The HPV33 L2 protein-derived polypeptide used in the embodiment of non-equal length substitution contains linker(s) of 1-3 amino acid(s) at its N-terminus and/or C-terminus.

Optionally, in the embodiment of non-equal length substitution, after the deletion of the amino acid 431-432 region of said HPV16 L1 protein or the mutant of the HPV16 L1 protein with a 31-amino-acid truncation at the C-terminus. The polypeptide of the amino acid sequence SEQ ID No. 2 or SEQ ID No. 3 is inserted between the amino acid 430 and 433 of said HPV16 L1 protein or the mutant of HPV16 L1 protein with a 31-amino-acid truncation at the C-terminus.

Another aspect of the present invention relates to a polynucleotide encoding the papillomavirus chimeric proteins described above.

The present invention also provides a vector comprising the polynucleotide as described above, and provides a host cell comprising the vector.

The sequences of the polynucleotide encoding the above-described papillomavirus chimeric proteins in present invention are compatible to different expression systems. Optionally, these nucleotide sequences are fully genetically optimized using $E.$ $coli$ codons, thus can be highly expressed in $E.$ $coli$ expression systems; or they are genetically optimized using insect cell codons and can be highly expressed in insect cell expression systems.

The present invention also provides a papillomavirus capsid protein polymer, preferably a chimeric pentamer or a chimeric VLP, comprising the chimeric PV protein described above, or being composed of the chimeric PV protein described above.

The present invention also provides a use of the above-described chimeric papillomavirus proteins, chimeric pentamers, or chimeric VLPs in the preparation of vaccines for preventing papillomavirus infections and infection-associated diseases.

The present invention also provides a vaccine for preventing papillomavirus infections and infection-associated diseases, which comprises the above-mentioned PV chimeric pentamer or chimeric VLP, adjuvants, and excipients or carriers for vaccine. Preferably, the vaccine comprises at least one type of VLPs or cVLPs derived from mucosal and/or cutaneous HPVs. In said vaccine, the dose of each VLP is an effective amount which is capable of eliciting protective immune responses respectively.

Optionally, the adjuvant is selected from human adjuvants; preferably, the adjuvant is selected from a composition comprising aluminum adjuvant, oil-in-water emulsion or water-in-oil emulsion, and TLR stimulant, a composition comprising aluminum hydroxide adjuvant or aluminum phosphate adjuvant, polyinosinic-polycytidic acid (poly IC) adjuvant and stabilizer, or a composition comprising MF59 adjuvant, poly IC adjuvant and stabilizer.

Explanation of Terms used in the Invention

According to the present invention, the term "insect cell expression system" includes insect cells, recombinant baculoviruses, recombinant Bacmid and expression vectors, wherein the insect cells are commercially available cells, exemplified by, but not limited to, Sf9, Sf21, High Five.

According to the present invention, the term "prokaryotic expression system" includes, but is not limited to, $E.$ $coli$ expression system, wherein the host strains of prokaryotic expression system are commercially available, exemplified by, but not limited to, BL21(DE3), BL21(DE3) plysS, C43(DE3), Rosetta-gami B (DE3).

According to the present invention, the term "full-length HPV16 L1 protein" includes, but is not limited to, the full-length L1 proteins with the same length as the protein ID. AAC09292.1 in the NCBI database.

The gene fragment of "truncated HPV16 L1 protein" refers to the gene with a deletion of nucleotides encoding one or more amino acids at the 5' end and/or the 3' end, compared to the wild type HPV16 L1 protein gene, wherein the full-length sequence of "wild type HPV 16 L1 protein" is, for example, but not limited to, the following sequences in the NCBI database: AAC09292.1, AIQ82817.1, AAC61736.1, etc.

According to the present invention, the term "excipients or carriers for vaccine" refers to one or more agents selected from the group consisting of, but not limited to, pH modifiers, surfactants, ionic strength enhancers. For example, pH adjusting agents are exemplified by, but not limited to, phosphate buffers. Surfactants include cationic, anionic, or nonionic surfactants, for example, but not limited to, polysorbate 80 (Tween-80). Ionic strength enhancers include, but are not limited to sodium chloride.

According to the present invention, the term "human adjuvant" refers to the adjuvants which are clinically applicable to the human body, including various adjuvants which are currently approved and which may be approved in the future, such as, but not limited to aluminum adjuvants, MF59 and various forms of adjuvant compositions.

According to the present invention, the term "emulsion" refers to a heterogeneous liquid dispersion formed by mixing an aqueous phase component, an oil phase component and an emulsifier in an appropriate ratio and being emulsified. The aqueous phase components include, but are not limited to, buffer systems such as phosphate buffers, HEPES buffers, and the like; oil phase components are metabolizable lipids including, but not limited to, vegetable oils, fish oils, animal oils, synthetic oils and other lipidic components (such as, but not limited to squalene and tocopherol); and emulsifiers are suitable surfactants, such as, but are not limited to, sorbitan trioleate (Span-85) and polysorbate 80 (Tween-80).

According to the present invention, the term "stabilizer" refers to a component that binds to and stabilizes with poly IC in an adjuvant, which includes, but is not limited to, antibiotics (such as but not limited to kanamycin, Neomycin, gentamicin), inorganic salts (such as, but not limited to, calcium chloride, magnesium chloride, calcium phosphate), and cationic organic complexes (such as but not limited to calcium stearate and calcium gluconate).

According to the present invention, the vaccines of the present invention may be in a form acceptable to a patient, including but not limited to oral or injection, preferably injection.

According to the present invention, the vaccine of the present invention is preferably used in a unit dosage form, in which the dosage of VLP in the unit dosage form is 5-100 µg, preferably 30-60 µg.

DESCRIPTION OF THE DRAWINGS

FIG. 1A-1B: Expression of chimeric proteins in $E.$ $coli$ and insect cells described in Example 5. The results showed that all the 12 chimeric proteins could be highly expressed in $E.$ $coli$ or insect cells.

FIG. 2A-2B: DLS analysis of purified cVLPs described in Example 6. The results showed that the hydrodynamic diameters of HPV16L1ΔCDE$_{135-138}$/33dE and HPV16L1ΔCDE$_{135-138}$/33dEs were 91.6 nm and 97.9 nm respectively. The chimeric proteins were 100% assembled into VLPs.

FIG. 2A: HPV16L1ΔCDE$_{135-138}$/33dE; FIG. 2B: HPV16L1ΔCDE$_{135-138}$/33dEs

FIG. 3A-3F: Transmission electron microscopy (TEM) analysis of purified cVLPs described in Example 7. A large number of VLPs were observed in the field of view. The particles were quite uniform in size. The cVLPs comprising L2 polypeptide in DE region were about 50 nm in diameter, which is similar to the diameter of VLP of L1 protein. The cVLPs comprising L2 polypeptide in h4 region were smaller in diameter, about 35-40 nm. Bar=200 nm.

DETAILED DESCRIPTION OF THE INVENTION

The present invention will now be further illustrated by the following non-limiting examples. It is well known to those skilled in the art that many modifications may be made to the present invention without departing from the spirit of the invention. Such modifications are also within the scope of the invention. The following examples are only illustrative of the present invention and should not be construed as limiting the scope of the invention, since the embodiments are necessarily varied. The terminology used in this specification is for the purpose of illustrating particular embodiments only, and is not to be taken by way of limitation. The scope of the invention is defined in the appended claims.

Unless otherwise specified, all technical and scientific terms used herein have the same meaning as commonly understood by those skilled in the art to which this invention belongs. The preferred methods and materials of the present invention are described below, but any methods and materials similar or equivalent to those described in this invention may be used to practice or test the present invention. The following methods unless otherwise specified, are the conventional methods or methods described in the specification of products. Experimental materials used in the absence of special instructions, can be readily obtained from commercial companies. All publications mentioned in this specification are hereby incorporated by reference to disclose and describe the methods and/or materials in the publications.

EXAMPLE 1

Synthesis of the Genes of Chimeric L1 Proteins and the Construction of the Expression Vectors 12 chimeric L1 proteins are listed below:

1) Chimeric L1 protein HPV16 L1DE$_{136-137}$/33dE: The scaffold of HPV16 L1DE$_{136-137}$/33dE is full-length HPV16 L1 protein (sequence shown as SEQ ID No. 4), and aa. 16-37 polypeptide of HPV33 L2 protein was directly inserted into the DE loop of HPV16 L1 protein between aa. 136/137 (insertion sequence shown as SEQ ID No. 1). The polynucleotide encoding HPV16 L1DE$_{136-137}$/33dE was optimized according to the codon usage preference of $E.$ $coli$, and the coding sequence was constructed by inserting $E.$ $coli$ codon-optimized gene of HPV33 L2 protein aa. 16-37 (sequence shown as SEQ ID No. 9) between nucleotide (nt.) 408/409 of $E.$ $coli$ codon-optimized HPV16 L1 scaffold gene (sequence shown as SEQ ID No. 8).

2) Chimeric L1 protein HPV16 L1DE$_{136-137}$/33dEs: The scaffold of HPV16 L1DE$_{136-137}$/33dEs is full-length HPV16 L1 protein (sequence shown as SEQ ID No. 4), and aa. 17-32 polypeptide of HPV33 L2 protein was directly inserted into the DE loop of HPV16 L1 protein between aa. 136/137 (insertion sequence shown as SEQ ID No. 2). The polynucleotide encoding HPV16 L1DE$_{136-137}$/33dEs was optimized according to the codon usage preference of E. coli, and the coding sequence was constructed by inserting E. coli codon-optimized gene of HPV33 L2 protein aa. 17-32 (sequence shown as SEQ ID No.10) between nt.408/409 of E. coli codon-optimized HPV16 L1 scaffold gene (sequence shown as SEQ ID No. 8).

3) Chimeric L1 protein HPV16 L1DE$_{135-138}$/33dE: The scaffold of HPV16 L1DE$_{135-138}$/33dE is full-length HPV16 L1 protein (sequence shown as SEQ ID No. 4), and aa. 135-139 region of HPV16 L1 protein was substituted by the aa. 16-37 polypeptide of HPV33 L2 protein, which contains linkers, i.e. the aa. 16-37 polypeptide with linkers was inserted into the HPV16 L1 protein between aa. 134/139 by non-equal length substitution, the amino acid sequence of the inserted fragment was shown as SEQ ID No. 5, wherein the N-terminal linker of HPV33 L2 aa. 16-37 polypeptide was G (glycine) P (proline) linker, and the C-terminal linker was P (proline) linker. The polynucleotide encoding HPV16 L1DE$_{135-138}$/33dE was optimized according to the codon usage preference of *E. coli*, and the coding sequence was constructed by deleting nt.403-414 from *E. coli* codon-optimized HPV16 L1 gene (sequence shown as SEQ ID No. 8), and inserting sequence SEQ ID No.11 between nt.402/415 of the codon-optimized HPV16 L1 gene.

4) Chimeric L1 protein HPV16 L1DE$_{135-138}$/33dEs: The scaffold of HPV16 L1DE$_{135-138}$/33dEs is full-length HPV16 L1 protein (sequence shown as SEQ ID No. 4), and aa. 135-139 region of HPV16 L1 protein was substituted by the aa. 17-32 polypeptide of HPV33 L2 protein, which contains linkers, i.e. aa. 17-32 polypeptide with linkers was inserted into the HPV16 L1 protein between aa. 134/139 by non-equal-length substitution, the amino acid sequence of the inserted fragment was shown as SEQ ID No. 6, wherein the N-terminal linker of HPV33 L2 aa. 17-32 polypeptide was G (glycine) P (proline) linker, and the C-terminal linker was P (proline) linker. The polynucleotide encoding HPV16 L1DE$_{135-138}$/33dEs was optimized according to the codon usage preference of *E. coli*, and the coding sequence was constructed by deleting nt.403-414 from *E. coli* codon-optimized HPV16 L1 gene (sequence shown as SEQ ID No. 8), and inserting sequence SEQ ID No.12 between nt.402/415 of the codon-optimized HPV16 L1 gene.

5) Chimeric L1 protein HPV16 L1h4/33dE: The scaffold of HPV16 L1h4/33dE is full-length HPV16 L1 protein (sequence shown as SEQ ID No. 4), and aa. 17-37 polypeptide of HPV33 L2 protein was inserted into the aa. 430-433 region of HPV16 L1 h4 region by non-equal length substitution. That is deleting the aa. 431-432 region from HPV16 L1 protein, and fusing the aa. 17-37 polypeptide with linkers between aa. 430/434 of HPV16 L1 protein. The amino acid sequence of the inserted fragment was shown as SEQ ID No. 3. The polynucleotide encoding HPV16 L1h4/33dE was optimized according to the codon usage preference of *E. coli*, and the coding sequence was constructed by deleting nt. 1291-1296 from *E. coli* codon-optimized HPV16 L1 gene (sequence shown as SEQ ID No. 8), and inserting sequence SEQ ID No.13 between nt. 1290/1297 of codon-optimized HPV16 L1 gene.

6) Chimeric L1 protein HPV16 L1h4/33dEs: The scaffold of HPV16 L1h4/33dE is full-length HPV16 L1 protein (sequence shown as SEQ ID No. 4), and aa. 17-32 polypeptide of HPV33 L2 protein was inserted into the aa. 430-433 region of HPV16 L1 h4 region by non-equal length substitution. That is deleting the aa. 431-432 region from HPV16 L1 protein, and fusing the aa. 17-32 polypeptide with linkers between aa. 430/434 of HPV16 L1. The amino acid sequence of inserted fragment was shown as SEQ ID No. 2. The polynucleotide coding for HPV16 L1h4/33dEs was optimized according to the codon usage preference of *E. coli*, and the coding sequence was constructed by deleting nt. 1291-1296 from *E. coli* codon-optimized HPV16 L1 gene (sequence shown as SEQ ID No. 8), and inserting sequence SEQ ID No.10 between nt. 1290/1297 of codon-optimized HPV16 L1 gene.

7) Chimeric L1 protein HPV16L1ΔCDE$_{136-137}$/33dE: The scaffold of HPV16L1ΔCDE$_{136-137}$/33dE is C-terminal truncated HPV16 L1 protein (deleting 31 amino acids from the sequence shown as SEQ ID No. 4 at the C-terminus), and aa. 16-37 polypeptide of HPV33 L2 protein was directly inserted into the DE loop of truncated HPV16 L1 protein between aa. 136/137 (insertion sequence shown as SEQ ID No. 1). The polynucleotide encoding HPV16 L1ΔCDE$_{136-137}$/33dE was optimized according to the codon usage preference of insect cells, and the coding sequence was constructed by inserting insect cell codon-optimized gene of HPV33 L2 protein aa. 16-37 (sequence shown as SEQ ID No.15) between nt.408/409 of insect cell codon-optimized HPV16 L1 scaffold gene (sequence shown as SEQ ID No. 14).

8) Chimeric L1 protein HPV16 L1ΔCDE$_{136-137}$/33dEs: The scaffold of HPV16 L1ΔCDE$_{136-137}$/33dEs is C-terminal truncated HPV16 L1 protein (deleting 31 amino acids from the sequence shown as SEQ ID No. 4 at the C-terminus), and aa. 17-32 polypeptide of HPV33 L2 protein was directly inserted into the DE loop of truncated HPV16 L1 protein between aa. 136/137 (insertion sequence shown as SEQ ID No. 2). The polynucleotide encoding HPV16L1ΔCDE$_{136-137}$/33dEs was optimized according to the codon usage preference of insect cells, and the coding sequence was constructed by inserting insect cell codon-optimized gene of HPV33 L2 protein aa. 17-32 (sequence shown as SEQ ID No.16) between nt.408/409 of insect cell codon-optimized HPV16 L1 scaffold gene (sequence shown as SEQ ID No. 14).

9) Chimeric L1 protein HPV16 L1ΔCDE$_{135-138}$/33dE: The scaffold of HPV16 L1ΔCDE$_{135-138}$/33dE is C-terminal truncated HPV16 L1 protein (deleting 31 amino acids from sequence shown as SEQ ID No. 4 at the C-terminus), and aa. 135-139 region of the truncated HPV16 L1 protein was substituted by the aa. 16-37 polypeptide of HPV33 L2 protein, which contains linkers, i.e. the aa. 16-37 polypeptide with linkers was inserted into the truncated HPV16 L1 protein between aa. 134/139 by non-equal length substitution, the amino acid sequence of inserted fragment was shown as SEQ ID No. 5, wherein the N-terminal linker of HPV33 L2 aa. 16-37 polypeptide was G (glycine) P (proline) linker, and the C-terminal linker was P (proline) linker. The polynucleotide encoding HPV16 L1ΔCDE$_{135-138}$/33dE was optimized according to the codon usage preference of insect cells, and the coding sequence was constructed by deleting nt.403-414 from the insect cell codon-optimized HPV16 L1 gene (sequence shown as SEQ ID No. 14), and inserting sequence SEQ ID No.17 between nt.402/415 of the codon-optimized HPV16 L1 gene.

10) Chimeric L1 protein HPV16 L1ΔCDE$_{135-138}$/33dEs: The scaffold of HPV16 L1ΔCDE$_{135-138}$/33dEs is C-terminal truncated HPV16 L1 protein (deleting 31 amino acids from the sequence shown as SEQ ID No. 4 at the C-terminus), and aa. 135-139 region of the truncated HPV16 L1 protein was substituted by aa. 17-32 polypeptide of HPV33 L2 protein, which contains linkers, i.e. aa. 17-32 polypeptide with linkers was inserted into the truncated HPV16 L1 between aa. 134/139 by non-equal length substitution, the amino acid sequence of inserted fragment was shown as SEQ ID No. 6, wherein the N-terminal linker of HPV33 L2 aa. 17-32 polypeptide was G (glycine) P (proline) linker, and the C-terminal linker was P (proline) linker. The polynucleotide encoding HPV16 L1ΔCDE$_{135-138}$/33dEs was optimized according to the codon usage preference of insect cells, and the coding sequence was constructed by deleting nt.403-414 from the insect cell codon-optimized HPV16 L1 gene (sequence shown as SEQ ID No. 14), and inserting sequence SEQ ID No.18 between nt.402/415 of the codon-optimized HPV16 L1 gene.

11) Chimeric L1 protein HPV16 L1ΔCh4/33dE: The scaffold of HPV16L1 ΔCh4/33dE is C-terminal truncated HPV16 L1 protein (deleting 31 amino acids from the sequence shown as SEQ ID No. 4 at the C-terminus), and aa. 17-37 polypeptide of HPV33 L2 protein was inserted into the aa. 430-433 region of truncated HPV16 L1 h4 region by non-equal length substitution. That is deleting the aa. 431-433 region from HPV16 L1 protein, and fusing the aa. 17-37 polypeptide of HPV33 L2 protein between aa. 430/434 of truncated HPV16 L1. The amino acid sequence of inserted fragment was shown as SEQ ID No. 3. The polynucleotide encoding HPV 16L1ΔCh4/33dE was optimized according to the codon usage preference of insect cells, and the coding sequence was constructed by deleting nt. 1291-1296 from insect cell codon-optimized HPV16 L1 gene (sequence shown as SEQ ID No. 14), and inserting sequence SEQ ID No. 19 between nt. 1290/1297 of the codon-optimized HPV16 L1 gene.

12) Chimeric L1 protein HPV16 L1ΔCh4/33dEs: The scaffold of HPV16 L1ΔCh4/33dEs is C-terminal truncated HPV16 L1 protein (deleting 31 amino acids from the sequence shown as SEQ ID No. 4 at the C-terminus of), and aa. 17-32 polypeptide of HPV33 L2 protein was inserted into the aa. 430-433 region of truncated HPV16 L1 h4 region by non-equal length substitution. That is deleting the aa. 431-432 region of HPV16 L1 protein, and fusing aa. 17-32 polypeptide of HPV33 L2 protein between aa. 430/434 of truncated HPV16 L1 protein. The amino acid sequence of inserted fragment was shown as SEQ ID No. 2. The polynucleotide coding for HPV16 L1ΔCh4/33dEs was optimized according to the codon usage preference of insect cells, and the coding sequence was constructed by deleting nt. 1291-1296 from insect cell codon-optimized HPV16 L1 gene (sequence shown as SEQ ID No. 14), and inserting sequence SEQ ID No. 16 between nt. 1290/1297 of the codon-optimized HPV16 L1 gene.

Chimeric L1 genes were optimized according to the codon usage preference of E. coli or insect cells respectively, and optimized genes were synthesized by Sangon Biotech (Shanghai) Co., Ltd.

Each gene optimized according to codon usage preference of E. coli was digested by NdeI/XhoI enzymes, and were inserted into commercially available expression vector pET22b (Novagen). Each gene optimized according to codon usage preference of insect cells were digested by EcoRI/XbaI enzymes and were inserted into commercially available expression vector pFastBac1 (Invitrogen). The resulting recombinant chimeric L1 gene expression vectors were listed below: pET22b-16L1DE$_{136-137}$/33dE; pET22b-16L1DE$_{136-137}$/33dEs; pET22b-16L1DE$_{135-138}$/33dE; pET22b-16L1DE$_{135-138}$/33dEs; pET22b-16L1h4/33dE; pET22b-16L1h4/33dEs; pFastBac1-16L1ΔCDE$_{136-137}$/33dE; pFastBac 1-16L1ΔCDE$_{136-137}$/33dEs; pFastBac 1-16L1ΔCDE$_{135-138}$/33dE; pFastBac 1-16L1ΔCDE$_{135-138}$/33dEs; pFastBac1-16L1ΔCh4/33dE; pFastBac1-16L1ΔCh4/33dEs. Methods of digestion, ligation, and cloning used above are disclosed and are described, for example, in patent CN 101293918 B.

EXAMPLE 2

Construction of the Recombinant Bacmids and Recombinant Baculoviruses Containing the Chimeric L1 Protein Genes E. coli DH10BAC competent cells were transformed with recombinant expression vectors containing the chimeric L1 genes (pFastBac 1-16L1ΔCDE$_{136-137}$/33dE, pFastBac1-16L1ΔCDE$_{136-137}$/33dEs, pFastBac 1-16L1ΔCDE$_{135-138}$/33dE, pFastBac1-16L1ΔCDE$_{135-138}$/33dEs, pFastBac1-16L1ΔCh4/33dE, pFastBac1-16L1ΔCh4/33dEs), and recombinant bacmids were selected. The recombinant baculoviruses were then produced by transfecting Sf9 cells with the selected recombinant bacmids which propagating in the Sf9 cells. Methods of recombinant bacmid selection and recombinant baculovirus production are well-known and are described, for example, in patent CN101148661 B.

EXAMPLE 3

Expression of Chimeric L1 Protein Genes in Sf9 Cells

Sf9 cells were infected with recombinant baculoviruses containing the above mentioned 6 chimeric L1 genes respectively, and the expression of the chimeric L1 proteins was carried out. The cells were cultured for 88 hours at 27° C., and were harvested by centrifuging at 3000 rpm for 15 min, and the supernatant was discarded. The cell pellets were washed with PBS and then used for expression analysis and purification. Methods of infection and expression are disclosed, for example, in patent CN 101148661 B.

EXAMPLE 4

Expression of Chimeric L1 Protein Genes in E. coli

E. coli BL21(DE3) competent cells were transformed with recombinant expression vectors containing the chimeric L1 genes (pET22b-16L1DE$_{136-137}$/33dE, pET22b-16L1DE$_{136-137}$/33dEs, pET22b-16L1DE$_{135-138}$/33dE, pET22b-16L1DE$_{135-138}$/33dEs, pET22b-16L1h4/33dE, pET22b-16L1h4/33dEs).

The transformed clones were inoculated into 3 ml of LB medium containing ampicillin and cultured overnight at 37° C. The overnight culture was added to LB medium at the ratio of 1:100, incubated at 37° C. for about 3 hours, until the OD600 reached 0.8-1.0. Then IPTG was added to medium at a final concentration of 0.5 μM. The cells were cultured at 16° C. for 12 h, and then were harvested by centrifugation.

EXAMPLE 5

Expression Analysis of Chimeric L1 Protein

Figure 1A:
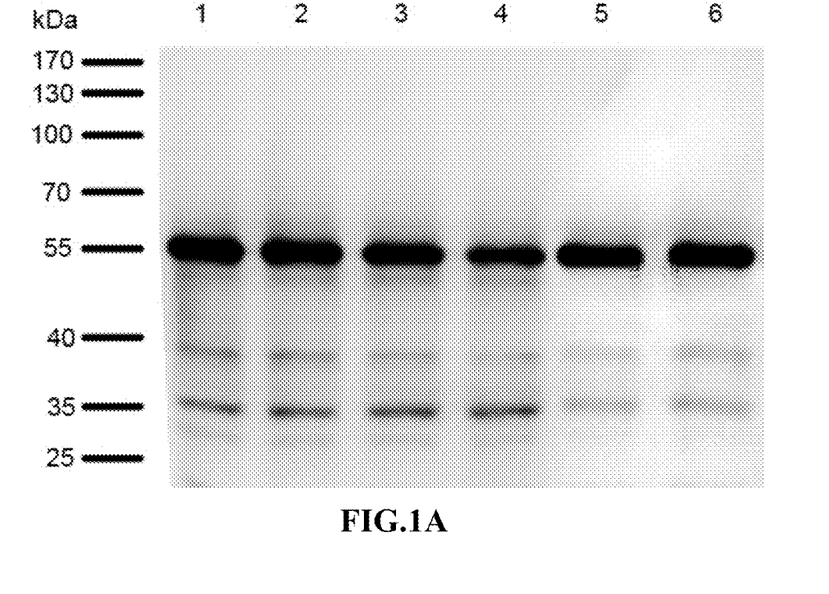
FIG. 1A: Expression of chimeric proteins in $E.$ $coli$. Lane 1. HPV16L1DE$_{136-137}$/33dE; Lane 2. HPV16L1DE$_{136-137}$/33dEs; Lane 3. HPV16L1DE$_{135-138}$/33dE; Lane 4. HPV16L1DE$_{135-138}$/33dEs; Lane 5. HPV16L1h4/33dE; Lane 6. HPV16L1h4/33dEs.
Figure 1B:
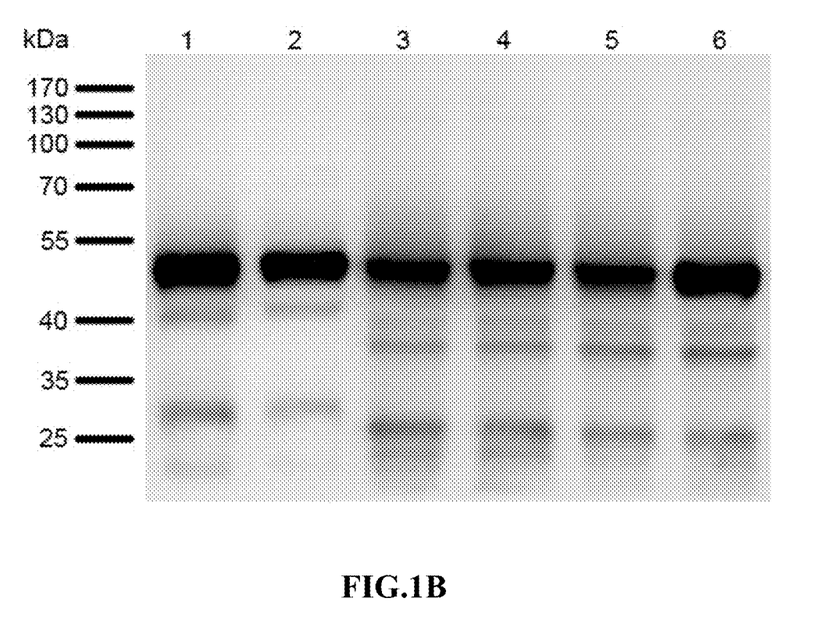
FIG. 1B: Expression of chimeric proteins in insect cells. Lane 1. HPV16L1ΔCDE$_{136-137}$/33dE; Lane 2. HPV16L1ΔCDE$_{136-137}$/33dEs; Lane 3. HPV16L1ΔCDE$_{135-138}$/33dE; Lane 4. HPV16L1ΔCDE$_{135-138}$/33dEs; Lane 5. HPV16L1ΔCh4/33dE; Lane 6. HPV16L1ΔCh4/33dEs.

Cells expressing different chimeric L1 proteins described in Example 3 and Example 4 were resuspended with PBS at a concentration of 1×10⁶ cells/200 µl PBS and mixed with 50 µl 6× Loading Buffer. Then the mixture was denatured at 75° C. for 8 min 10 µl of denatured samples were loaded for SDS-PAGE and Western blotting analysis respectively. The results were shown in FIG. 1. All 12 recombinant chimeric L1 proteins were expressed effectively in *E. coli* or insect cells expression system. The molecular weight of HPV16L1DE$_{136\text{-}137}$/33dE, HPV 16L1DE$_{136\text{-}137}$/33dEs, HPV16L1DE$_{135\text{-}138}$/33dE, HPV16L1DE$_{135\text{-}138}$/33dEs, HPV16L1h4/33dE, HPV16L1h4/33dEs was about 55 kDa, and that of the other 6 chimeric proteins was about 50 kDa. Methods of SDS-PAGE and Western blotting are disclosed, for example, in patent CN101148661 B.

EXAMPLE 6

Purification of Chimeric L1 Protein and Dynamic Light Scattering Analysis (DLS) of the Particle Size Proper amount of cells expressing chimeric L1 were resuspended in 10 ml PBS. PMSF was added to a final concentration of 1 mg/ml, and cells were ruptured by ultrasonic (Ningbo Xinzhi Ultrasonic Breaker, 6# probe, 200 W, ultrasonic for 5 s, followed by an interval of 7 s, for a total duration of 10 min). The lysate was used for purification at room temperature. VLPs were depolymerized by adding 4% β-mercaptoethanol (w/w) to the lysate, and the sample was then filtered using a 0.22 µm filter followed by purifying with DMAE anion exchange chromatography or CM cation exchange chromatography (elution with 20 mM Tris, 180 mM NaCl, 4% β-ME, pH 7.9), TMAE anion exchange chromatography or Q cation exchange chromatography (elution with 20 mM Tris, 180 mM NaCl, 4% β-ME, pH 7.9) and hydroxyapatite chromatography (elution with 100 mM NaH$_2$PO$_4$, 30 mM NaCl, 4% β-ME, pH 6.0), sequentially. The purified product was concentrated using a Planova ultrafiltration system and VLPs were assembled by buffer exchanging (20 mM NaH$_2$PO$_4$, 500 mM NaCl, pH 6.0). The above purification methods are disclosed, for example, in patents CN101293918 B, CN1976718 A and the like.

Figure 2A:
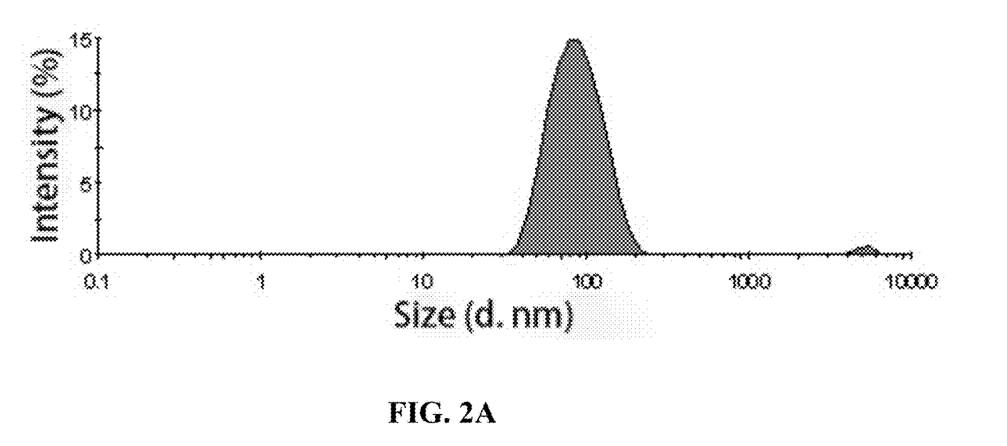
Figure 2B:
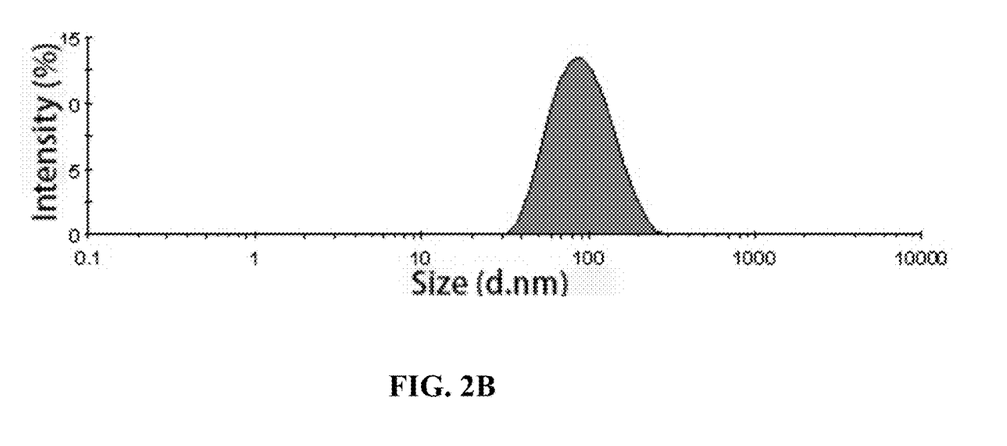
Figure 3A:
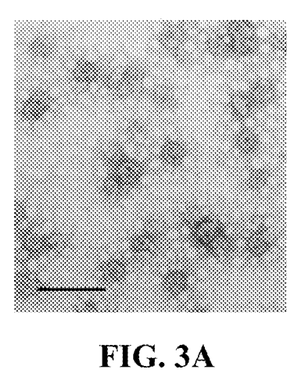
FIG. 3A: HPV16L1ΔCDE$_{136-137}$/33DE.
Figure 3B:
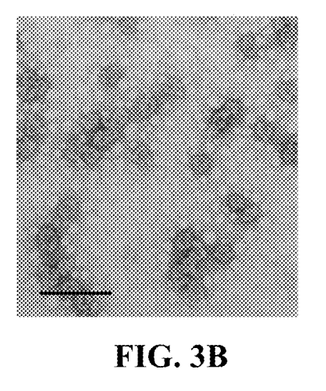
FIG. 3B: HPV16L1ΔCDE$_{136-137}$/33dEs.
Figure 3C:
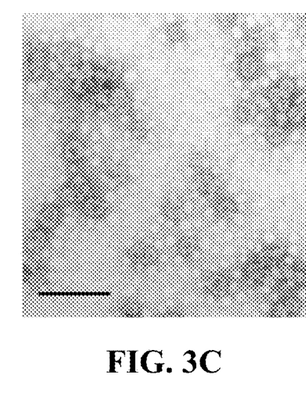
FIG. 3C: HPV16L1ΔCDE$_{135-138}$/33DE.
Figure 3D:
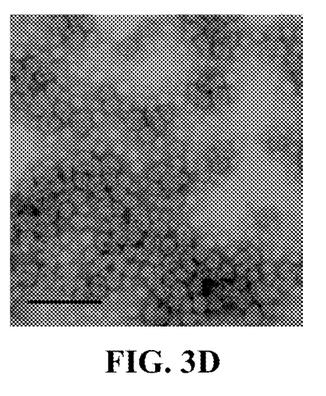
FIG. 3D: HPV16L1ΔCDE$_{135-138}$/33dEs.
Figure 3E:
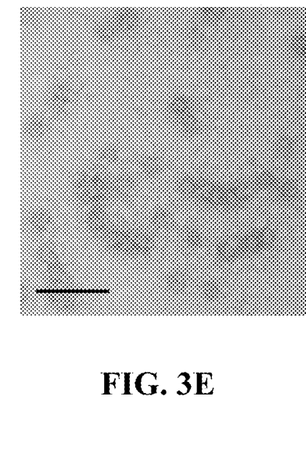
FIG. 3E: HPV16L1ΔCh4/33DE.
Figure 3F:
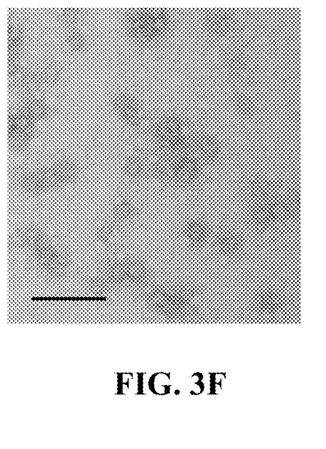
FIG. 3F: HPV16L1ΔCh4/33dEs.

The purified chimeric protein solution was subjected to DLS particle size analysis (Zetasizer Nano ZS 90 Dynamic Light Scattering Instrument, Malvern). The results are shown in Table 1, and the DLS analysis of HPV16L1ΔCDE$_{135\text{-}138}$/33dE and HPV16L1ΔCDE$_{135\text{-}138}$/33dEs was shown in FIG. 2.

TABLE 1

DLS analysis of chimeric L1 proteins

| Proteins | Hydrodynamic diameter (nm) | PDI |
|---|---|---|
| HPV16L1DE$_{136\text{-}137}$/33dE | 92.5 | 0.131 |
| HPV16L1DE$_{136\text{-}137}$/33dEs | 98.4 | 0.142 |
| HPV16L1DE$_{135\text{-}138}$/33dE | 91.4 | 0.133 |
| HPV16L1DE$_{135\text{-}138}$/33dEs | 95.2 | 0.142 |
| HPV16L1h4/33dE | 89.4 | 0.176 |
| HPV16L1h4/33dEs | 82.6 | 0.188 |
| HPV16L1ΔCDE$_{136\text{-}137}$/33dE | 99.4 | 0.142 |
| HPV16L1ΔCDE$_{136\text{-}137}$/33dEs | 98.8 | 0.136 |
| HPV16L1ΔCDE$_{135\text{-}138}$/33dE | 91.6 | 0.177 |
| HPV16L1ΔCDE$_{135\text{-}138}$/33dEs | 97.9 | 0.143 |
| HPV16L1ΔCh4/33dE | 88.6 | 0.144 |
| HPV16L1ΔCh4/33dEs | 90.8 | 0.152 |

EXAMPLE 7

Observation of Chimeric VLPs by Transmission Electron Microscope (TEM)

The chimeric VLPs were respectively purified using the chromatographic purification methods described in Example 6 and the dialyzed VLPs were used to prepare a copper mesh and stained with 1% uranyl acetate. After dried thoroughly, VLPs were observed with JEM-1400 electron microscope (Olympus). As shown in FIG. 3, the insect-cell-expressed chimeric cVLPs comprising L2 polypeptide in DE loop were about 50 nm in diameter, whereas cVLPs comprising L2 polypeptide in h4 region were about 35-40 nm in diameter. Diameters of Prokaryotic expressed cVLPs were consistent with that of cVLPs expressed in insect cells, cVLPs comprising L2 polypeptide in DE loop were about 50 nm in diameter, and cVLPs comprising L2 polypeptide in h4 region were about 35-40 nm in diameter. Methods of preparing copper mesh and electron microscopy are disclosed, for example, in patent CN 101148661 B.

EXAMPLE 8

Immunization of Chimeric VLPs and Detection of Neutralizing Antibody Titers

Four-to-six-week old BALB/c mice were randomly divided into groups, 5 mice per group. The mice were immunized subcutaneously with 10 µg of cVLP, 50 µg of Al(OH)$_3$ adjuvant and 50 µg of PIKA adjuvant at weeks 0, 2, 4 and 6 for 4 times. Sera were collected 2 weeks after the fourth immunization through the tail vein.

Twelve types of HPV pseudoviruses were used to detect the neutralizing antibody titers of immune sera. As shown in Table 2, the results showed that cVLPs expressed in either insect cells or *E. coli* cells effectively induced broad-spectrum cross-neutralizing antibodies in mice, among which the immune sera of HPV16L1ΔCDE$_{136\text{-}137}$/33dE and other insect-cell-expressed cVLPs can neutralize at least 12 types of pseudoviruses. Methods for pseudovirus preparation and pseudovirus neutralization assay are disclosed, for example, in patent CN 104418942A.

Moreover, chimeric proteins constructed by inserting L2 epitopes with other flexible linkers in the DE region or the h4 region included in the present invention can assemble into cVLPs. When immunizing mice using the above-mentioned strategy, these cVLPs induced comparable levels of cross-neutralizing antibodies to the cVLPs shown in Table 2. The pentamers composed of the above-mentioned 12 chimeric L1 proteins also induced cross-neutralizing antibodies in mice when using the above-mentioned immunization strategy.

TABLE 2

| | | Type Of pseudo-virus | | | | | |
|---|---|---|---|---|---|---|---|
| Name of Anti-sera | | HPV16 L1ΔCDE$_{136-137}$/ 33dE VLP | HPV16 L1ΔCDE$_{136-137}$/ 33dEs VLP | HPV16 L1ΔCDE$_{135-138}$/ 33dE VLP | HPV16 L1ΔCDE$_{135-138}$/ 33dEs VLP | HPV16 L1ΔC h4/ 33dE VLP | HPV16 L1ΔC h4/ 33dEs VLP |
| Mean neutralizing antibody titers | HPV16 | 128000 | 165800 | 128000 | 140800 | 211200 | 160400 |
| | HPV31 | 25 | 50 | 50 | 25 | 25 | 25 |
| | HPV33 | 1350 | 2400 | 1325 | 2600 | 1350 | 1100 |
| | HPV35 | 100 | 150 | 112.5 | 100 | 150 | 100 |
| | HPV52 | 150 | 125 | 137.5 | 212.5 | 100 | 125 |
| | HPV58 | 1350 | 800 | 2450 | 1100 | 500 | 600 |
| | HPV18 | 250 | 200 | 300 | 350 | 150 | 200 |
| | HPV39 | 200 | 300 | 500 | 225 | 0-25 | 25 |
| | HPV45 | 300 | 250 | 400 | 337.5 | 100 | 125 |
| | HPV68 | 100 | 125 | 100 | 212.5 | 0-25 | 25 |
| | HPV6 | 500 | 400 | 600 | 412.5 | 175 | 150 |
| | HPV5 | 450 | 500 | 525 | 450 | 0-25 | 25 |

Neutralizing antibody titers induced by different cVLP in mice

What is claimed is:

1. A chimeric papillomavirus protein, comprising: a papillomavirus HPV16 L1 protein or a mutant of the papillomavirus HPV16 L1 protein as a scaffold; and at least one polypeptide from a HPV33 L2 protein or from a mutant of the HFV33 L2 protein inserted into the scaffold, wherein
    the at least one polypeptide is shown as SEQ ID NO: 1, SEQ ID NO: 2, SEQ ID NO: 3, SEQ ID NO: 5, or SEQ ID NO: 6,
    the at least one polypeptide is inserted into a surface region of the HPV16 L1 protein or the mutant of the HPV16 L1 protein, and
    the at least one polypeptide is selected from the group consisting of:
    the polypeptide from the HPV33 L2 protein shown as SEQ ID NO: 1 or SEQ ID NO: 2 is inserted into the HPV16 L1 protein or the mutant of the HPV16 L1 protein between amino acid positions 136 and 137, after deletion of amino acid 135-138 region from the HPV16 L1 protein or the mutant of the HPV16 L1 protein, the polypeptide from the HPV33 L2 protein shown as SEQ ID NO: 5 or SEQ ID NO: 6 is inserted into the HPV16 L1 protein or the mutant of the HPV16 L1 protein between amino acid positions 134 and 139, and after deletion of amino acid 431-432 region from the HPV16 L1 protein or the mutant of the HPV16 L1 protein, the polypeptide from the HPV33 L2 protein shown as SEQ ID NO: 2 or SEQ ID NO: 3 is inserted into the HPV16 L1 protein or the mutant of the HPV16 L1 protein between amino acid positions 430 and 433.

2. The chimeric papillomavirus protein according to claim 1, wherein the HPV16 L1 protein or the mutant of the HPV16 L1 protein is shown as SEQ ID NO: 4 or the amino acid sequence of SEQ ID NO: 4 with 31 amino acid deletion at the C-terminus.

3. A polynucleotide encoding the chimeric papillomavirus protein according to claim 1.

4. A polymer composed of papillomavirus capsid protein, wherein the polymer is a chimeric pentamer or chimeric virus-like particle, which contains the chimeric papillomavirus protein of claim 1 or is consisted of the chimeric papillomavirus protein of claim 1.

5. A method for preventing HPV infection or HPV infection-associated diseases, comprising administering a prophylactically effective amount of the chimeric papillomavirus protein of one of claims 1 and 2 or the chimeric pentamer or chimeric virus-like particle of claim 4 to a subject.

6. A vaccine for preventing papillomavirus infection or infection-associated diseases, comprising the polymer of claim 4, adjuvants, and excipients or vehicles for the vaccine.

7. The polynucleotide of claim 3, wherein the sequence of the polynucleotide is optimized according to the codon usage preference of *E. coli* or insect cells.

8. The vaccine of claim 6, further comprising at least one virus-like particle or chimeric virus-like particle derived from mucosal and/or cutaneous HPV.

9. The vaccine of claim 6, wherein the adjuvant is a human adjuvant.

10. The vaccine of claim 9, wherein the human adjuvant is a composition selected from the group consisting of: a composition comprising Alum adjuvant, oil-in-water emulsion or water-in-oil emulsion and TLR agonist, a composition comprising aluminum hydroxide adjuvant or aluminum phosphate adjuvant, polyinosinic-polycytidic acid adjuvant and stabilizing agent, and a composition comprising MF59 adjuvant, polyinosinic-polycytidic acid adjuvant and stabilizing agent.

11. A vector comprising the polynucleotide of claim 3 or claim 7.

12. An isolated host cell comprising the vector of claim 11.

* * * * *

SEQUENCE LISTING

<160> NUMBER OF SEQ ID NOS: 19

<210> SEQ ID NO 1
<211> LENGTH: 22
<212> TYPE: PRT
<213> ORGANISM: Human papillomavirus type 33

<400> SEQUENCE: 1

Gln Leu Tyr Gln Thr Cys Lys Ala Thr Gly Thr Cys Pro Pro Asp Val
1               5                   10                  15

Ile Pro Lys Val Glu Gly
            20

<210> SEQ ID NO 2
<211> LENGTH: 16
<212> TYPE: PRT
<213> ORGANISM: Human papillomavirus type 33

<400> SEQUENCE: 2

Leu Tyr Gln Thr Cys Lys Ala Thr Gly Thr Cys Pro Pro Asp Val Ile
1               5                   10                  15

<210> SEQ ID NO 3
<211> LENGTH: 21
<212> TYPE: PRT
<213> ORGANISM: Human papillomavirus type 33

<400> SEQUENCE: 3

Leu Tyr Gln Thr Cys Lys Ala Thr Gly Thr Cys Pro Pro Asp Val Ile
1               5                   10                  15

Pro Lys Val Glu Gly
            20

<210> SEQ ID NO 4
<211> LENGTH: 505
<212> TYPE: PRT
<213> ORGANISM: Human papillomavirus type 16

<400> SEQUENCE: 4

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn

```
            20                  25                  30
Ile Tyr Tyr His Ala Gly Thr Ser Arg Leu Leu Ala Val Gly His Pro
        35                  40                  45
Tyr Phe Pro Ile Lys Lys Pro Asn Asn Asn Lys Ile Leu Val Pro Lys
 50                  55                  60
Val Ser Gly Leu Gln Tyr Arg Val Phe Arg Ile His Leu Pro Asp Pro
 65                  70                  75                  80
Asn Lys Phe Gly Phe Pro Asp Thr Ser Phe Tyr Asn Pro Asp Thr Gln
                 85                  90                  95
Arg Leu Val Trp Ala Cys Val Gly Val Glu Val Gly Arg Gly Gln Pro
                100                 105                 110
Leu Gly Val Gly Ile Ser Gly His Pro Leu Leu Asn Lys Leu Asp Asp
            115                 120                 125
Thr Glu Asn Ala Ser Ala Tyr Ala Ala Asn Ala Gly Val Asp Asn Arg
            130                 135                 140
Glu Cys Ile Ser Met Asp Tyr Lys Gln Thr Gln Leu Cys Leu Ile Gly
145                 150                 155                 160
Cys Lys Pro Pro Ile Gly Glu His Trp Gly Lys Gly Ser Pro Cys Thr
                165                 170                 175
Asn Val Ala Val Asn Pro Gly Asp Cys Pro Pro Leu Glu Leu Ile Asn
                180                 185                 190
Thr Val Ile Gln Asp Gly Asp Met Val Asp Thr Gly Phe Gly Ala Met
            195                 200                 205
Asp Phe Thr Thr Leu Gln Ala Asn Lys Ser Glu Val Pro Leu Asp Ile
            210                 215                 220
Cys Thr Ser Ile Cys Lys Tyr Pro Asp Tyr Ile Lys Met Val Ser Glu
225                 230                 235                 240
Pro Tyr Gly Asp Ser Leu Phe Phe Tyr Leu Arg Arg Glu Gln Met Phe
                245                 250                 255
Val Arg His Leu Phe Asn Arg Ala Gly Ala Val Gly Glu Asn Val Pro
                260                 265                 270
Asp Asp Leu Tyr Ile Lys Gly Ser Gly Ser Thr Ala Asn Leu Ala Ser
            275                 280                 285
Ser Asn Tyr Phe Pro Thr Pro Ser Gly Ser Met Val Thr Ser Asp Ala
290                 295                 300
Gln Ile Phe Asn Lys Pro Tyr Trp Leu Gln Arg Ala Gln Gly His Asn
305                 310                 315                 320
Asn Gly Ile Cys Trp Gly Asn Gln Leu Phe Val Thr Val Val Asp Thr
                325                 330                 335
Thr Arg Ser Thr Asn Met Ser Leu Cys Ala Ala Ile Ser Thr Ser Glu
            340                 345                 350
Thr Thr Tyr Lys Asn Thr Asn Phe Lys Glu Tyr Leu Arg His Gly Glu
            355                 360                 365
Glu Tyr Asp Leu Gln Phe Ile Phe Gln Leu Cys Lys Ile Thr Leu Thr
            370                 375                 380
Ala Asp Val Met Thr Tyr Ile His Ser Met Asn Ser Thr Ile Leu Glu
385                 390                 395                 400
Asp Trp Asn Phe Gly Leu Gln Pro Pro Gly Gly Thr Leu Glu Asp
                405                 410                 415
Thr Tyr Arg Phe Val Thr Ser Gln Ala Ile Ala Cys Gln Lys His Thr
            420                 425                 430
Pro Pro Ala Pro Lys Glu Asp Pro Leu Lys Lys Tyr Thr Phe Trp Glu
            435                 440                 445
```

```
Val Asn Leu Lys Glu Lys Phe Ser Ala Asp Leu Asp Gln Phe Pro Leu
    450                 455                 460
Gly Arg Lys Phe Leu Leu Gln Ala Gly Leu Lys Ala Lys Pro Lys Phe
465                 470                 475                 480
Thr Leu Gly Lys Arg Lys Ala Thr Pro Thr Thr Ser Ser Thr Ser Thr
                485                 490                 495
Thr Ala Lys Arg Lys Arg Lys Leu
            500                 505

<210> SEQ ID NO 5
<211> LENGTH: 25
<212> TYPE: PRT
<213> ORGANISM: Artificial Sequence
<220> FEATURE:
<223> OTHER INFORMATION: HPV 33 L2 aa. 16-37 with linkers

<400> SEQUENCE: 5

Gly Pro Gln Leu Tyr Gln Thr Cys Lys Ala Thr Gly Thr Cys Pro Pro
1               5                   10                  15
Asp Val Ile Pro Lys Val Glu Gly Pro
            20                  25

<210> SEQ ID NO 6
<211> LENGTH: 19
<212> TYPE: PRT
<213> ORGANISM: Artificial Sequence
<220> FEATURE:
<223> OTHER INFORMATION: HPV 33 L2 aa. 17-32 with linkers

<400> SEQUENCE: 6

Gly Pro Leu Tyr Gln Thr Cys Lys Ala Thr Gly Thr Cys Pro Pro Asp
1               5                   10                  15
Val Ile Pro

<210> SEQ ID NO 7
<211> LENGTH: 467
<212> TYPE: PRT
<213> ORGANISM: Human papillomavirus type 33

<400> SEQUENCE: 7

Met Arg His Lys Arg Ser Thr Arg Arg Lys Arg Ala Ser Ala Thr Gln
1               5                   10                  15
Leu Tyr Gln Thr Cys Lys Ala Thr Gly Thr Cys Pro Pro Asp Val Ile
            20                  25                  30
Pro Lys Val Glu Gly Ser Thr Ile Ala Asp Gln Ile Leu Lys Tyr Gly
        35                  40                  45
Ser Leu Gly Val Phe Phe Gly Gly Leu Gly Ile Gly Thr Gly Ser Gly
    50                  55                  60
Ser Gly Gly Arg Thr Gly Tyr Val Pro Ile Gly Thr Asp Pro Pro Thr
65                  70                  75                  80
Ala Ala Ile Pro Leu Gln Pro Ile Arg Pro Pro Val Thr Val Asp Thr
                85                  90                  95
Val Gly Pro Leu Asp Ser Ser Ile Val Ser Leu Ile Glu Glu Thr Ser
            100                 105                 110
Phe Ile Glu Ala Gly Ala Pro Ala Pro Ser Ile Pro Thr Pro Ser Gly
        115                 120                 125
Phe Asp Val Thr Thr Ser Ala Asp Thr Thr Pro Ala Ile Ile Asn Val
    130                 135                 140
```

Ser Ser Val Gly Glu Ser Ile Gln Thr Ile Ser Thr His Leu Asn
145                 150                 155                 160

Pro Thr Phe Thr Glu Pro Ser Val Leu His Pro Pro Ala Pro Glu
                165                 170                 175

Ala Ser Gly His Phe Ile Phe Ser Ser Pro Thr Val Ser Thr Gln Ser
            180                 185                 190

Tyr Glu Asn Ile Pro Met Asp Thr Phe Val Val Ser Thr Asp Ser Ser
            195                 200                 205

Asn Val Thr Ser Ser Thr Pro Ile Pro Gly Ser Arg Pro Val Ala Arg
            210                 215                 220

Leu Gly Leu Tyr Ser Arg Asn Thr Gln Gln Val Lys Val Val Asp Pro
225                 230                 235                 240

Ala Phe Leu Thr Ser Pro His Lys Leu Ile Thr Tyr Asp Asn Pro Ala
                245                 250                 255

Phe Glu Ser Phe Asp Pro Glu Asp Thr Leu Gln Phe Gln His Ser Asp
                260                 265                 270

Ile Ser Pro Ala Pro Asp Pro Asp Phe Leu Asp Ile Ile Ala Leu His
            275                 280                 285

Arg Pro Ala Ile Thr Ser Arg Arg His Thr Val Arg Phe Ser Arg Val
290                 295                 300

Gly Gln Lys Ala Thr Leu Lys Thr Arg Ser Gly Lys Gln Ile Gly Ala
305                 310                 315                 320

Arg Ile His Tyr Tyr Gln Asp Leu Ser Pro Ile Val Pro Leu Asp His
                325                 330                 335

Thr Val Pro Asn Glu Gln Tyr Glu Leu Gln Pro Leu His Asp Thr Ser
                340                 345                 350

Thr Ser Ser Tyr Ser Ile Asn Asp Gly Leu Tyr Asp Val Tyr Ala Asp
            355                 360                 365

Asp Val Asp Asn Val His Thr Pro Met Gln His Ser Tyr Ser Thr Phe
370                 375                 380

Ala Thr Thr Arg Thr Ser Asn Val Ser Ile Pro Leu Asn Thr Gly Phe
385                 390                 395                 400

Asp Thr Pro Val Met Ser Gly Pro Asp Ile Pro Ser Pro Leu Phe Pro
                405                 410                 415

Thr Ser Ser Pro Phe Val Pro Ile Ser Pro Phe Phe Pro Phe Asp Thr
            420                 425                 430

Ile Val Val Asp Gly Ala Asp Phe Val Leu His Pro Ser Tyr Phe Ile
            435                 440                 445

Leu Arg Arg Arg Arg Lys Arg Phe Pro Tyr Phe Phe Thr Asp Val Arg
450                 455                 460

Val Ala Ala
465

<210> SEQ ID NO 8
<211> LENGTH: 1518
<212> TYPE: DNA
<213> ORGANISM: Artificial Sequence
<220> FEATURE:
<223> OTHER INFORMATION: prokaryotic codon-optimized HPV16 L1
      full-length gene

<400> SEQUENCE: 8
atgagcctgt ggttacctag cgaagctacc gtttatttgc cgccggtccc ggtgtcgaaa    60
gtggtgagca ccgatgagta tgtcgcccgt accaatattt attaccatgc gggtacgtcg   120
cgcctgctcg cggtaggcca cccgtatttt ccgatcaaaa aaccaaacaa taacaagatt   180

```
ctggtgccga aagttagtgg tctgcaatat cgcgtgttcc ggattcattt acctgacccg      240
aataaatttg ggttcccgga tactagcttt tataacccgg acacccagcg cttggtgtgg      300
gcgtgcgtgg gtgttgaagt cggccgtgga caaccgcttg gcgtaggtat ctctggccac      360
ccgctcctga ataaactgga tgacaccgag aacgcctccg catacgcggc taatgccggc      420
gtggataacc gtgaatgcat cagcatggac tataagcaga cgcaattatg tttgattggg      480
tgcaaaccac cgatcggtga acattggggc aaaggttcgc cttgcaccaa tgttgcggtg      540
aacccgggcg attgcccacc gctggaactg attaataccg tgattcagga cggtgatatg      600
gtggacacag gcttcggagc gatggatttt acgacgctgc aagctaacaa aagtgaagtt      660
ccgctggata tctgtaccag catctgcaag tatccggatt atattaaaat ggtcagcgaa      720
ccgtacgggg actcgttatt cttttatttg cgccgcgagc agatgttcgt acggcacctt      780
tttaatcgcg ccggtgcagt gggcgaaaac gtgccggatg acctgtatat caaaggcagc      840
ggctcgaccg cgaatctggc gagtagcaac tatttcccta cgccgtctgg ttccatggtg      900
actagcgatg cccaaatttt taataaacca tactggctgc agcgtgcaca aggccataac      960
aatggcattt gttgggggaa ccagttattc gtaaccgtgg ttgacaccac gcgttcgacg     1020
aatatgagtt tgtgcgcggc tatcagcacc tctgagacca cgtataagaa cacgaatttt     1080
aaagaatacc tgcgccacgg tgaggaatat gatctccaat tcatctttca gctgtgtaaa     1140
attaccctga ccgccgatgt catgacgtat atccattcga tgaacagcac gattttagaa     1200
gattggaatt tcggcttgca accgcctccg ggcgggaccc ttgaagcaca atatcgtttt     1260
gtaacgtcgc aggcaattgc gtgccaaaaa cacactccac cggcgcctaa ggaggatccg     1320
ctcaaaaagt acaccttctg ggaagtgaac ctgaaagaga aatttagtgc cgatctggat     1380
cagttcccgt taggtcggaa attttgctg caagcaggcc tcaaggcgaa accgaaattc      1440
accctgggta aacgcaaggc tacgccgacg accagctcta cctccacgac ggccaaacgt     1500
aagaaacgta agctgtaa                                                   1518
```

<210> SEQ ID NO 9
<211> LENGTH: 66
<212> TYPE: DNA
<213> ORGANISM: Artificial Sequence
<220> FEATURE:
<223> OTHER INFORMATION: prokaryotic codon-optimized gene of HPV 33 L2
      aa. 16-37

<400> SEQUENCE: 9

```
cagctgtatc agacctgcaa agcgaccggt acctgcccgc cagatgtgat tccgaaagtg      60
gaaggt                                                                66
```

<210> SEQ ID NO 10
<211> LENGTH: 48
<212> TYPE: DNA
<213> ORGANISM: Artificial Sequence
<220> FEATURE:
<223> OTHER INFORMATION: prokaryotic codon-optimized gene of HPV 33 L2
      aa. 17-32

<400> SEQUENCE: 10

```
ctgtatcaga cctgcaaagc gaccggtacc tgcccgccag atgtgatc                   48
```

<210> SEQ ID NO 11
<211> LENGTH: 75
<212> TYPE: DNA

<213> ORGANISM: Artificial Sequence
<220> FEATURE:
<223> OTHER INFORMATION: prokaryotic codon-optimized gene of HPV 33 L2
      aa. 16-37with linkers

<400> SEQUENCE: 11

```
ggcccgcagc tgtatcagac ctgcaaagcg accggtacct gcccgccaga tgtgattccg    60
aaagtggaag gtccg                                                     75
```

<210> SEQ ID NO 12
<211> LENGTH: 57
<212> TYPE: DNA
<213> ORGANISM: Artificial Sequence
<220> FEATURE:
<223> OTHER INFORMATION: prokaryotic codon-optimized gene of HPV 33 L2
      aa. 17-32 with linkers

<400> SEQUENCE: 12

```
ggcccgctgt atcagacctg caaagcgacc ggtacctgcc cgccagatgt gatcccg       57
```

<210> SEQ ID NO 13
<211> LENGTH: 63
<212> TYPE: DNA
<213> ORGANISM: Artificial Sequence
<220> FEATURE:
<223> OTHER INFORMATION: prokaryotic codon-optimized gene of HPV 33 L2
      aa. 17-37

<400> SEQUENCE: 13

```
ctgtatcaga cctgcaaagc gaccggtacc tgcccgccag atgtgattcc gaaagtggaa    60
ggt                                                                  63
```

<210> SEQ ID NO 14
<211> LENGTH: 1426
<212> TYPE: DNA
<213> ORGANISM: Artificial Sequence
<220> FEATURE:
<223> OTHER INFORMATION: insect cell codon-optimized HPV 16 L1-delta-C
      gene

<400> SEQUENCE: 14

```
atgtccctct ggttgccatc cgaagctaca gtctatctcc caccagtccc agtcagtaaa    60
gttgttagta cagatgaata tgtcgctagg acaaacatct actaccatgc tggcacaagt   120
aggctcctcg ctgtcggcca cccatacttc cccatcaaga gcccaacaa caacaagatc    180 ctggtcccca aggtgagcgg cctgcagtat cgcgtgttcc gcatccacct gcccgatcca   240
aacaaattcg gcttccccga taagcttca tacaaccccg acacccaaag actcgtctgg   300
gcatgcgtgg gcgtcgaagt gggcaggggc caacccctgg gcgtcggtat ctccggtcac   360
cccctgctga caagctcga cgataccgag aacgcctccg cctacgctgc aacgctggc    420 gtcgacaacc gcgagtgcat cagcatggac tataagcaga cccagctctg cctgatcggc   480
tgtaagcccc ccatcggtga gcattgggt aaaggcagtc cctgcacaaa cgtcgctgtg   540
aaccccggtg actgccccc cctggaactg atcaataccg tcatccaaga cggtgacatg   600
gtcgacaccg gtttcggtgc catggatttc accaccctgc aagccaacaa gtccgaggtc   660
cccctcgaca tctgcaccag catctgtaag taccccgact acatcaagat ggtctccgag   720
ccctacggtg attcactgtt cttctacctg aggcgcgagc agatgttcgt ccgccacctg   780
ttcaaccgcg ctggcgctgt cggtgagaac gtgcccgatg acctgtatat caagggtagc   840
ggtagcaccg ccaacctggc atccagcaac tacttcccca cccctccggg cagcatggtc   900
```

```
acaagcgacg cacagatctt taacaagccc tactggctgc agagggccca aggtcataac    960
aacggtatct gctggggcaa tcagttgttc gtcaccgtcg tcgacaccac caggtccacc   1020
aacatgagcc tgtgcgccgc aatcagcacc agcgagacca cctacaagaa caccaatttc   1080
aaagaatact tgaggcacgg tgaagagtac gacctgcaat tcatcttcca actctgtaag   1140
atcacactga ccgccgatgt catgacctac atccacagca tgaacagcac catcctcgaa   1200
gattggaact tcggcttgca gcccccaccc ggcggtacct tggaggacac ctaccgcttc   1260
gtgaccagtc aagccatcgc tgccagaag cacacccccc ccgccccaa ggaagaccca    1320 ttgaagaagt ataccttctg ggaagtgaac ctgaaagaga aattcagcgc tgatttggac   1380
caattcccac tgggaaggaa attcctgttg caagctggtc tctaat                 1426
```

<210> SEQ ID NO 15
<211> LENGTH: 66
<212> TYPE: DNA
<213> ORGANISM: Artificial Sequence
<220> FEATURE:
<223> OTHER INFORMATION: insect cell codon-optimized gene of HPV 33 L2
      aa. 16-37

<400> SEQUENCE: 15

```
cagctgtacc aaacttgcaa agccaccggc acatgcccac tgacgtcat ccctaaggtc     60 gaagga                                                               66
```

<210> SEQ ID NO 16
<211> LENGTH: 48
<212> TYPE: DNA
<213> ORGANISM: Artificial Sequence
<220> FEATURE:
<223> OTHER INFORMATION: insect cell codon-optimized gene of HPV 33 L2
      aa. 17-32

<400> SEQUENCE: 16

```
ctgtaccaaa cttgcaaagc caccggcaca tgcccacctg acgtcatc                 48
```

<210> SEQ ID NO 17
<211> LENGTH: 75
<212> TYPE: DNA
<213> ORGANISM: Artificial Sequence
<220> FEATURE:
<223> OTHER INFORMATION: insect cell codon-optimized gene of HPV 33 L2
      aa. 16-37 with linkers

<400> SEQUENCE: 17

```
ggtccacagc tgtaccaaac ttgcaaagcc accggcacat gcccacctga cgtcatccct    60
aaggtcgaag gacct                                                     75
```

<210> SEQ ID NO 18
<211> LENGTH: 57
<212> TYPE: DNA
<213> ORGANISM: Artificial Sequence
<220> FEATURE:
<223> OTHER INFORMATION: insect cell codon-optimized gene of HPV 33 L2
      aa. 17-32 with linkers

<400> SEQUENCE: 18

```
ggtccactgt accaaacttg caaagccacc ggcacatgcc cacctgacgt catccct       57
```

<210> SEQ ID NO 19
<211> LENGTH: 63
<212> TYPE: DNA

```
<213> ORGANISM: Artificial Sequence
<220> FEATURE:
<223> OTHER INFORMATION: insect cell codon-optimized gene of HPV 33 L2
      aa. 17-37

<400> SEQUENCE: 19
ctgtaccaaa cttgcaaagc caccggcaca tgcccacctg acgtcatccc taaggtcgaa    60
gga                                                                  63
```